(12) United States Patent
Parvin et al.

(10) Patent No.: US 8,059,001 B2
(45) Date of Patent: Nov. 15, 2011

(54) SYSTEM AND METHOD FOR AUTOMATIC QUALITY CONTROL OF CLINICAL DIAGNOSTIC PROCESSES

(75) Inventors: Curtis A. Parvin, McKinney, TX (US); John Yundt-Pacheco, Fairview, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 393 days.

(21) Appl. No.: 12/471,042

(22) Filed: May 22, 2009

(65) Prior Publication Data
US 2010/0295685 A1 Nov. 25, 2010

(51) Int. Cl.
*G08B 23/00* (2006.01)
(52) U.S. Cl. ............ 340/573.1; 702/179; 702/22; 436/8
(58) Field of Classification Search .............. 340/573.1, 340/3.3, 3.32, 3.42–3.43; 702/19, 21–25, 702/30–32, 81, 84, 179–181, 183; 436/8–19
See application file for complete search history.

(56) References Cited

U.S. PATENT DOCUMENTS

| | | | | |
|---|---|---|---|---|
| 5,233,545 A | * | 8/1993 | Ho et al. | 702/180 |
| 5,411,031 A | * | 5/1995 | Yomtov | 600/519 |
| 5,633,166 A | | 5/1997 | Westgard | |
| 5,861,548 A | * | 1/1999 | Melvin et al. | 73/52 |
| 5,937,364 A | * | 8/1999 | Westgard et al. | 702/83 |
| 6,063,028 A | * | 5/2000 | Luciano | 600/300 |
| 6,556,951 B1 | | 4/2003 | Deleo et al. | |
| 7,050,933 B2 | | 5/2006 | Parvin | |
| 7,203,619 B2 | | 4/2007 | Parvin | |
| 7,286,957 B2 | | 10/2007 | Parvin | |
| 7,299,153 B2 | | 11/2007 | Parvin | |
| 7,318,000 B2 | | 1/2008 | Parvin | |
| 2005/0222504 A1 | | 10/2005 | Otvos et al. | |
| 2007/0027648 A1 | | 2/2007 | Kowata | |
| 2007/0112858 A1 | | 5/2007 | Maughan et al. | |
| 2008/0186133 A1 | | 8/2008 | Parkhurst et al. | |
| 2009/0119047 A1 | | 5/2009 | Zelin et al. | |

OTHER PUBLICATIONS

"XM—Exponentially Weighted Moving Average", article, Beckman Coulter, Inc., Bulletin 9611, Technical Information; 16 pgs, 2006.

* cited by examiner

*Primary Examiner* — John A Tweel, Jr.
(74) *Attorney, Agent, or Firm* — Stinson Morrison Hecker LLP; Mark C. Young (57) ABSTRACT

A system and method to automatically implement quality control of a clinical diagnostic process are disclosed. Upon generation of an internal error flag, a confirmation rule automatically checks a questionable patient statistic alert by testing a quality control specimen, applying event-related quality control rules to the results of that test, and provides an alert to the operator only upon a confirmed patient signal. The automatic quality control process thus eliminates the uncertainty of operator reaction to an alert signal and implements the quality control run automatically, without operator intervention.

25 Claims, 3 Drawing Sheets

SYSTEM AND METHOD FOR AUTOMATIC QUALITY CONTROL OF CLINICAL DIAGNOSTIC PROCESSES

CROSS-REFERENCE TO RELATED APPLICATIONS

Not applicable

STATEMENT REGARDING FEDERALLY SPONSORED RESEARCH OR DEVELOPMENT

Not applicable.

BACKGROUND OF THE INVENTION

1. Field of the Invention

The present invention relates generally to clinical diagnostic processes, and more particularly to systems and methods for implementing quality control in clinical diagnostic processes.

2. Description of Related Art

Clinical diagnostic laboratories employ various schemes to control the clinical diagnostic process to ensure the accuracy of diagnostic results. In the United States, Westgard is a well-known scheme, with other schemes, such as RiliBAK, more common outside of the U.S. More recently developed patient-data based schemes, such as a Biometric Quality Control process as described in U.S. Pat. No. 7,203,619 are also becoming more widely used.

Regardless of the specific quality control (QC) process employed, a common characteristic of known QC processes is the requirement for operator intervention to initiate and/or conduct the quality control process. However, operator intervention to conduct the quality control process does not necessarily occur as necessary or when required due to a variety of reasons. For example, many labs may not understand how to apply the QC rules such that frequent error flags lead to indifference on the part of the test operator who may simply ignore the ostensible error and choose not to conduct a quality control process. Thus, a too high QC false rejection rate may lead to an operator ignoring a signal or indication that a quality control process run should be undertaken. A College of American Pathologists (CAP) Q-Probe study conducted in 1994 found that many laboratories respond to a QC error flag by merely repeating the control. No reasoned troubleshooting occurs unless the test operator is unsuccessful in getting the control value to fall within acceptable limits. Reasons identified in the study for not immediately troubleshooting included the perception that it is easier to re-test than troubleshoot, laziness, lack of knowledge, habit, and no accountability to troubleshoot correctly.

As addressed in the Biometric Quality Control process invention of U.S. Pat. No. 7,203,619, rather than accept that some type of error might be present in the test system when a statistical flag occurs, labs may move immediately to some form of remedy rather than troubleshooting. The basic premise is that the statistical control system they use creates too many unwarranted errors so they automatically assume the error flag is false. The quickest remedy in this environment is to get the control value within range. To do so, some labs may repeat the control in hopes that the next value will be within limits, repeat with fresh control product, check or repeat calibration, or make up fresh reagent. Sometimes limited troubleshooting may be employed, including, for example, testing of assayed control materials to detect systematic error, looking at a history of control outliers, and calling the manufacturer for guidance or word of any national performance trends. Each of these actions is taken without any reasonable justification other than one of them usually corrects the error at least temporarily. Typically, the most common causes of QC error flags include random error, environmental conditions, control range too tight or incorrectly calculated, reagent (lot change, deterioration, contamination), control problems, calibration, sampling error, instrument malfunction, and poor maintenance.

Laboratory staff typically consider troubleshooting to be complex and often unguided. The production atmosphere of a typical lab and limited resources may contribute to a philosophy of avoiding troubleshooting unless absolutely necessary. The assumption follows that if troubleshooting could be focused, guided, or deemed necessary and productive, laboratory staff would engage in the effort. In general, it is desirable to make troubleshooting far easier by, for example, providing a QC system that identifies actionable error (i.e., eliminates false error detection), providing online troubleshooting advice, providing interactive online user groups so labs can exchange information readily, basing analytical process control on medical relevance limits (where appropriate), providing an analysis of the most frequently observed errors and determining the most likely cause of the error flag, providing instrument-specific troubleshooting guides, posting control stability claims and interlabs online, providing method group statistics, providing continuing education, and providing parallel lots for troubleshooting.

Thus, it is apparent that current quality control processes relying on operator intervention suffer from numerous drawbacks, often leading to misapplication of the quality control process itself.

BRIEF SUMMARY OF THE INVENTION

The present invention is directed to an automatic quality control process that automatically checks a questionable patient statistic alert by automatically testing a quality control specimen, applying event-related quality control rules, and providing an alert to the operator only upon a confirmed patient signal. The automatic quality control process thus eliminates the uncertainty of operator reaction to an alert signal and implements the quality control run without operator intervention. In one aspect, the system and method of the present invention provide a Laboratory Information System (LIS) with an automatic quality control process, in another aspect, the system and method provide a laboratory workstation with an automatic quality control process, and in yet another aspect, the system and method provide a laboratory diagnostic instrument with an automatic quality control process. Thus, the automatic quality control system and method of the present invention can be used or implemented at any level of the laboratory testing environment.

The automatic quality control system and method of the present invention will be described herein in conjunction with the Biometric Quality Control process of U.S. Pat. No. 7,203,619 which is incorporated by reference herein in its entirety. However, it should be understood that the system and method of the present invention may equally be used with any other quality control process providing a signal or alert to an operator, such implementations are contemplated by and within the scope of the present invention.

Routine quality control involves the periodic testing of QC samples in order to detect an out-of-control error condition that may have occurred at any point in time. An accurate assessment of a routine QC strategy must account for the interplay between the size of an out-of-control error condition, the subsequent risk of producing unacceptable patient results, the frequency of QC testing, and the chance of rejecting a QC rule when it is applied. The Biometric Quality Control process described herein considers the expected number of unacceptable patient results due to an out-of-control error condition as an important outcome measure for QC performance. The Biometric Quality Control process identifies the optimal combination of frequency of QC testing, number of QCs tested, and QC rules applied in order to minimize the expected number of unacceptable patient results produced due to any out-of-control error condition that might occur. The Biometric Quality Control process uses modified EWMA (Exponentially Weighted Moving Averages) and CUSUM (Cumulative Sums) models that can be applied to population means and variances. EWMA, with modifications, is the primary mechanism to monitor both routine QC data and patient population data for mean and variance. CUSUM is provided as an alternative mechanism for those users who prefer CUSUM.

In using either the EWMA or CUSUM (or other QC process), exceeding an EWMA or CUSUM QC limit generates an internal patient alert signal that triggers the patient limit confirmation of the present invention. In response to the exceeded limit, the patient alert confirmation module identifies the instrument that produced the result, initiates a request for a quality control specimen evaluation, waits for the quality control specimen test results, and applies event-related quality control rules to the specimen results to determine whether the internal patient alert was accurate. If the internal patient alert is found to be accurate, a confirmed patient alert signal is generated, providing an indicator to the operator. If the internal patient alert is found to be inaccurate, no indicator is provided to the operator and testing of patient samples continues in a normal manner. Because the patient alert confirmation module automatically instigates a test of a quality control specimen upon the initial internal patient alert, no operator intervention is required. Thus, there is no delay in instigating the quality control test attributable to the operator. In addition, the operator cannot ignore the internal patient alert as could occur in prior art systems in which instigation of the quality control run was at the discretion of the operator.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings and claims. In the drawings, like reference numbers indicate identical or functionally similar elements.

DETAILED DESCRIPTION OF EXEMPLARY EMBODIMENTS

A system and method for automatic control of a clinical diagnostic process in accordance with exemplary embodiments of the present invention are depicted in FIGS. 1 through 5. While the invention and embodiments are described herein in conjunction with a Biometric Quality Control process, it should be understood that the invention may be used with other quality control processes and that the embodiments described herein are exemplary in nature and not limiting.

Figure 1:
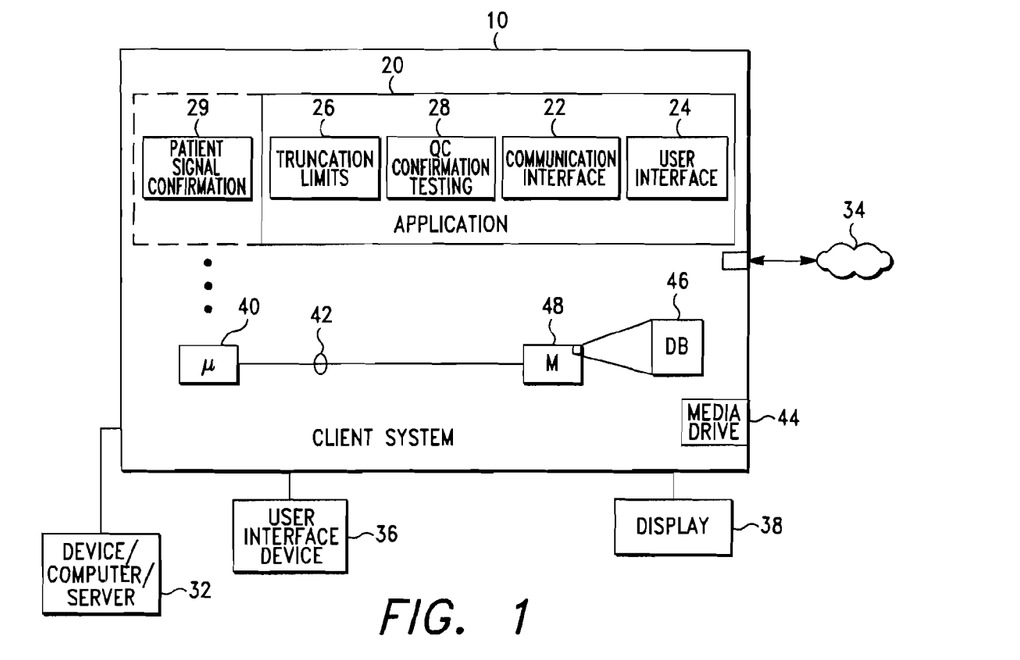
FIG. 1 depicts a block diagram of a client computer system configured with an automatic quality control patient signal confirmation application module according to a first exemplary embodiment the present invention.
Figure 2:
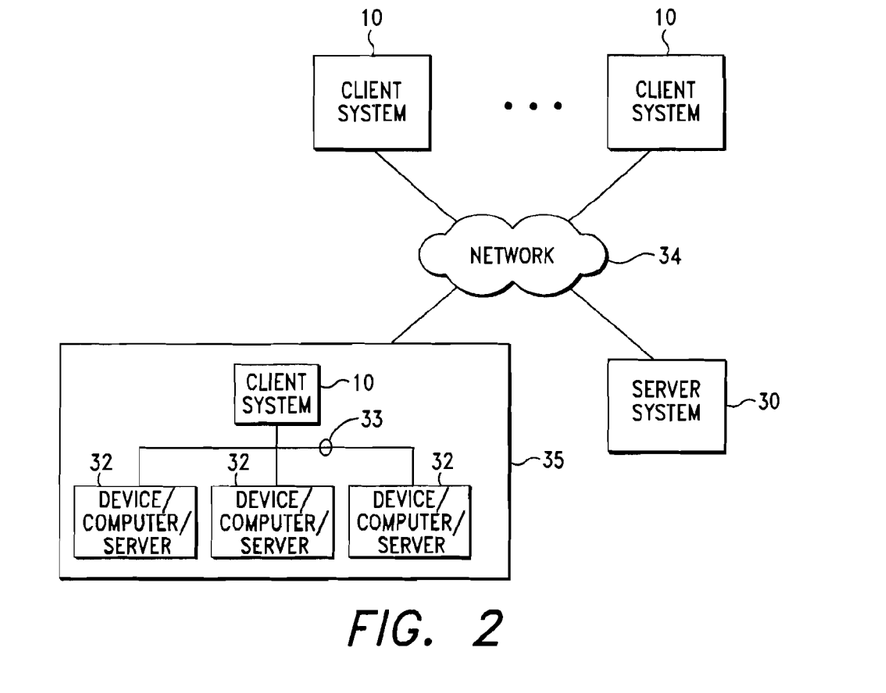
FIG. 2 depicts a block diagram of a network arrangement for executing a shared application and/or communicating data and commands between multiple computing systems and devices according to an exemplary embodiment of the present invention.

Looking first to FIGS. 1 and 2, a client computer system 10 is configured with a Biometric quality control (QC) application module 20 (also referred to herein as, for example, "QC application" or "QC module"). As best shown in FIG. 2, a plurality of client computer systems 10 may be arranged in network configuration for executing a shared application and/or for communicating data and commands between multiple computing systems and devices according to an exemplary embodiment of the present invention. Client computer system 10 may operate as a stand-alone system or it may be connected to a server system 30 and/or other client systems 10 and/or other devices/servers 32 over a network 34.

Several elements in the system depicted in FIGS. 1 and 2 are well-known, existing elements and variations of those exemplary elements may be implemented in accordance with the present invention. For example, client system 10 may include a desktop personal computer, a workstation, a laptop computer, a handheld mobile device, or any other computing device capable of executing the quality control application module 20. In client-server or networked embodiments, client system 10 is configured to interface directly or indirectly with server system 30 over network 34. Network 34 may be any type of network known in the art, such as a local area network (LAN), a wide area network (WAN), the Internet, an ad-hoc network, or any other type of network. Client system 10 may also communicate directly or indirectly with one or more other client systems 10 and devices/servers 32 over network 34. Client system 10 preferably executes a web browsing program, such as Microsoft's Internet Explorer, Netscape Navigator, Opera or the like, allowing a user of client system 10 to access, process and view information and pages available to it from server system 30 or other server systems over network 34. Client system 10 also preferably includes one or more user interface devices 36, such as a keyboard, a mouse, a touch screen, graphical tablet, pen or the like, for interacting with a graphical user interface (GUI) provided on a display 38. Display 38 is preferably a monitor or LCD screen, but may be any type of display device known in the art.

In one exemplary embodiment, Biometric QC application module 20 executes entirely on client system 10 (e.g., stand alone), however, in alternative embodiments the application module may be executed in a networked environment such as a client-server, peer-to-peer, or multi-computer networked environment where portions of the application code may be executed on different portions of the network system or where data and commands are exchanged between various components or devices executing portions of the application code. In local network embodiments, interconnection via a LAN is preferred, however, it should be understood that other networks can be used, such as the Internet or any intranet, extranet, virtual private network (VPN), non-TCP/IP based network, WAN or the like. For example, in the exemplary embodiment depicted in FIG. 2, a LAN 33 interconnects multiple devices to a client system 10. Such a network is exemplary of a multiple instrument environment 35, such as a laboratory or hospital, where multiple instruments, devices, or servers are connected to a client system 10 in a Laboratory Information System (LIS) arrangement. LAN 33 may include wireless and wired links and nodes, and use various communication protocols as are well known in the art.

Preferably, server system 30 acts as a central computer system that executes a majority of, or all, of the Biometric QC application module code, with each client system 10 acting as a terminal or log-in point for a user. For example, client system 10 may reside in a laboratory or a hospital multiple instrument environment 35 as part of a LIS, while server system 30 may reside in a geographically remote location. In such a configuration, Biometric QC application module code is preferably executed entirely on server system 30, with data and commands sent between client system 10 over network 34. For example, if client system 10 resides in a laboratory, client system 10 would provide the required patient data and/or test results/data, and other information from a local database and local instruments and devices for processing by server system 30, which would then provide processing results back to client system 10, or to other computer systems. It should be understood that the Biometric QC application code may execute entirely on a single system or portions may execute on both systems 10 and 30 (or on multiple systems in other exemplary embodiments) as desired for computational efficiency purposes. Additionally, a client system 10 in a multiple instrument environment 35 may execute a portion or all of the Biometric QC processing code.

Looking again to FIG. 1, in an exemplary embodiment, client system 10 and some or all of its components are operator configurable through operation of the Biometric QC application module 20, which includes computer code executable on a central processing unit 40 coupled to other components over one or more busses 42 as is well known in the art. Computer code, including instructions for operating and configuring client system 10 (or other systems on which the application module is executing, such as server system 30 of FIG. 2) to process data content, monitor and control QC processes, and render GUI images as described herein, is preferably stored on a hard disk, but the entire program code, or portions thereof, may also be stored in any other volatile or non-volatile memory medium or device as is well known, such as a ROM or RAM, or provided on any media capable of storing program code, such as a compact disk (CD) medium, digital versatile disk (DVD) medium, a floppy disk, and the like.

An appropriate media drive 44 is provided for receiving and reading documents, data and code from such a computer-readable medium. Additionally, the entire program code of module 20, or portions thereof, or related commands such as Active X commands, may be transmitted and downloaded from a software source, such as server system 30, to client system 10 or from another server system or computing device to client system 10 over the Internet as is well known, or transmitted over any other conventional network connection (e.g., extranet, VPN, LAN, etc.) using any communication medium and protocols (e.g., TCP/IP, HTTP, HTTPS, Ethernet, etc.) as are also well known. It should be understood that computer code for implementing aspects of the present invention can be implemented in a variety of coding languages such as C, C++, Java, Visual Basic, and others, or any scripting language, such as VBScript, JavaScript, Perl or markup languages such as XML, that can be executed on client system 10 and/or in a client server or networked arrangement. In addition, a variety of languages can be used in the external and internal storage of data, e.g., patient results, device and instrument information (e.g., IDs, date/time stamps, calibration information, temperature information, etc.), and other information, according to aspects of the present invention.

In an exemplary embodiment, Biometric QC application module 20 includes instructions for monitoring and controlling QC processes, as well as for providing user interface configuration capabilities, as described herein. Application module 20 is preferably downloaded and stored on media hard drive 44 (or other memory such as a local or attached RAM or ROM), although application module 20 can also be provided on any software storage medium such as a floppy disk, CD, DVD, etc. as discussed above.

In an exemplary embodiment as depicted in FIG. 1, application module 20 includes various software modules for processing data content. A communication interface module 22 is provided for communicating text and/or other data to a display driver for rendering images (e.g., GUI images) on display 38, and for communicating with device/server 32 and/or other computers or server systems in network embodiments. A user interface module 24 is provided for receiving user input, commands, and signals from user interface device 36. Communication interface module 22 preferably includes a browser application, which may be the same browser as the default browser configured on client system 10 as described previously, or any other browser or user interface application. Alternatively, interface module 22 includes the functionality to interface with a browser application executing on client system 10.

Application module 20 also includes a truncation limits module 26 including instructions to process patient data to determine truncation limits, a QC Confirmation testing module 28 including instructions to determine optimal QC rule(s), and a patient signal confirmation module 29 operable to monitor the results of the patient data QC testing and automatically perform quality control upon detection of an internal patient alert signal, each of which will be discussed in more detail below. The operation and execution of application module 20, viewed in its entirety, thus comprises a complete patient monitoring algorithm operable to review, monitor, and process patient data in accordance with the rules of the Biometric Quality Control process as described herein. As will also be discussed in more detail below, while patient signal confirmation module 29 is shown as operating in conjunction with the Biometric Quality Control application module, the patient signal confirmation module is not itself a part of the Biometric Quality control process, but operates in conjunction with and communicates with that process. Thus, while the patient signal confirmation module embodying the automatic quality control process of the present invention may be included in an instrument or system implementing a Biometric Quality Control process and may execute on a system in conjunction with the Biometric QC process (as depicted in the exemplary system of FIG. 1), or may even be coded into a single executable application with the Biometric QC process, the automatic quality control method of the present invention may also be used or implemented in conjunction with other quality control processes or in a stand-alone configuration, that is contemplated by and within the scope of the present invention.

Compiled statistics (e.g., device and instrument information), patient information, and other information are preferably stored in database 46, which may reside in memory 48, in a memory card or other memory or storage system such as an attached storage subsystem RAID drive system, for retrieval by truncation limits module 26, QC confirmation testing module 28, patient signal confirmation module 29, and other parts of Biometric QC application module 20. It should be appreciated that application module 20, or portions thereof, as well as appropriate data can be downloaded to and executed on client system 10.

Figure 3:
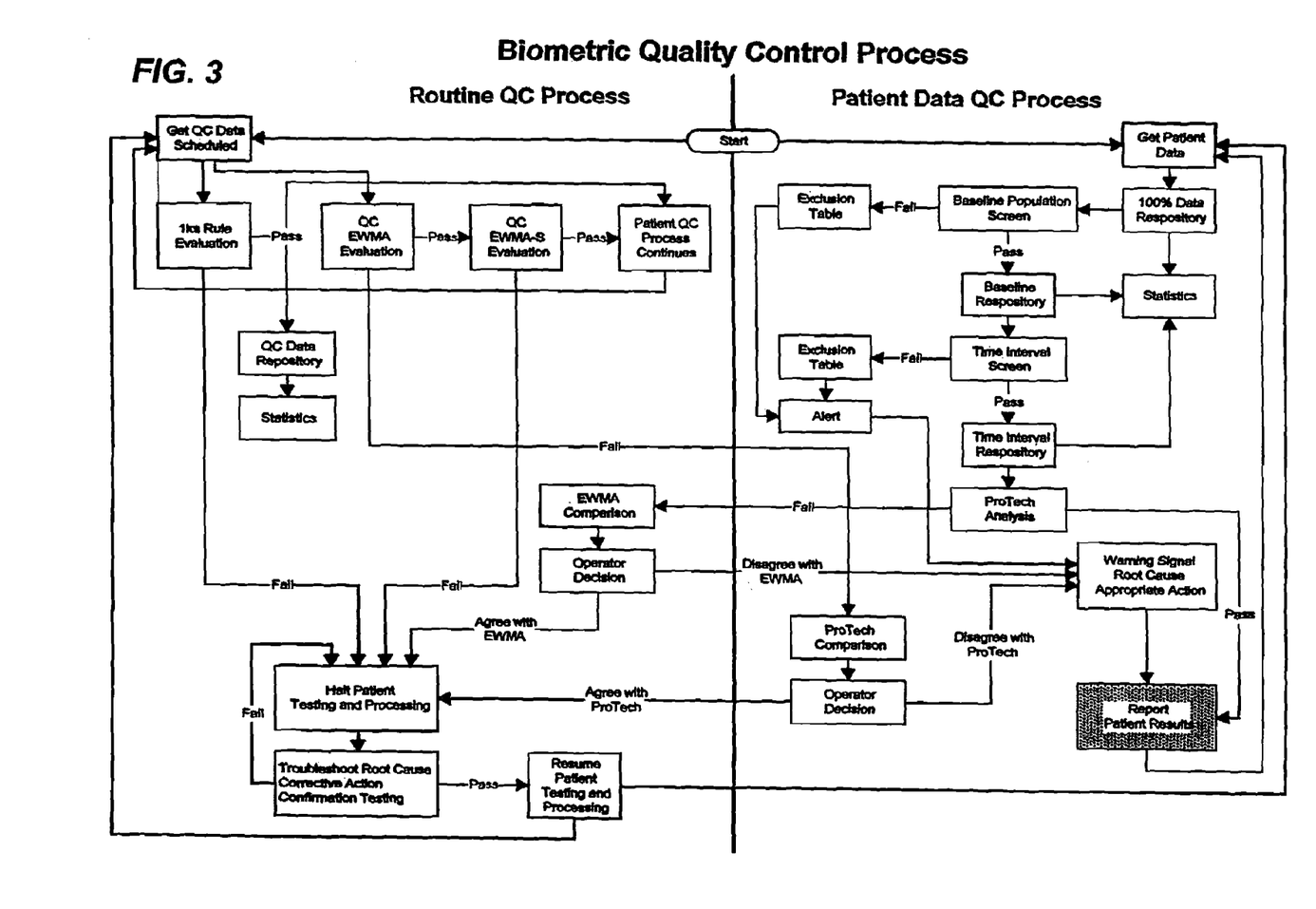
FIG. 3 depicts a block diagram of a Biometric Quality Control system in a clinical diagnostic process configured to communicate with an automatic quality control system according to an exemplary embodiment of the present invention.

FIG. 3 illustrates a general overview of an exemplary QC process implemented by Biometric QC application 20 according to an exemplary embodiment of the present invention. The process depicted in FIG. 3 is useful for monitoring instrument and test data and identifying preliminary indications of the need for instrument maintenance or calibration.

As will be described in more detail below, those preliminary indications trigger an initial alert to the patient signal confirmation module 29 which then performs further analysis and review of the alert and patient data and instigates an automatic quality control process before either: (1) confirming the initial alert signal (in which case an external alert to the operator is generated) or (2) determining that the initial alert signal was in error (in which case the initial alert signal is reset and the QC testing process is resumed).

Looking still to FIG. 3, in preferred aspects, a QC model and a patient-based data model are used to quantify the reliability of the testing platform. Preferably the two models are based on EWMA protocols, however, CUSUM may also be used. For example, in one embodiment, routine QC testing is monitored by a single rule based on laboratory quality goals. Preferably a 1 ks rule (e.g., 13 s rule) using a standard Shewhart (Levey-Jennings) chart, or a mean/SD rule using a normalized scale, is used. The patient based model allows the system to identify the source of a shift in performance of an instrument or device. Shifts in performance are a common problem in laboratories and may be based on a variety of factors including for example, an artifact of the control product, instrument malfunction and reagent impurity.

As depicted in FIG. 3, the various rules and paths of analyzing and monitoring the data can result in one or more error flags indicating an out-of-control condition, an exceeded limit, or other error condition are designated in the block diagram by labels at various blocks within the flow diagram as "fail", "halt patient testing and processing", "troubleshoot root cause, corrective action, confirmation testing", "alert", or "warning signal". As described above, in prior art systems these alerts or warnings are often ignored by the operators, particularly when numerous signals perceived as "nuisance" signals are generated.

Figure 4:
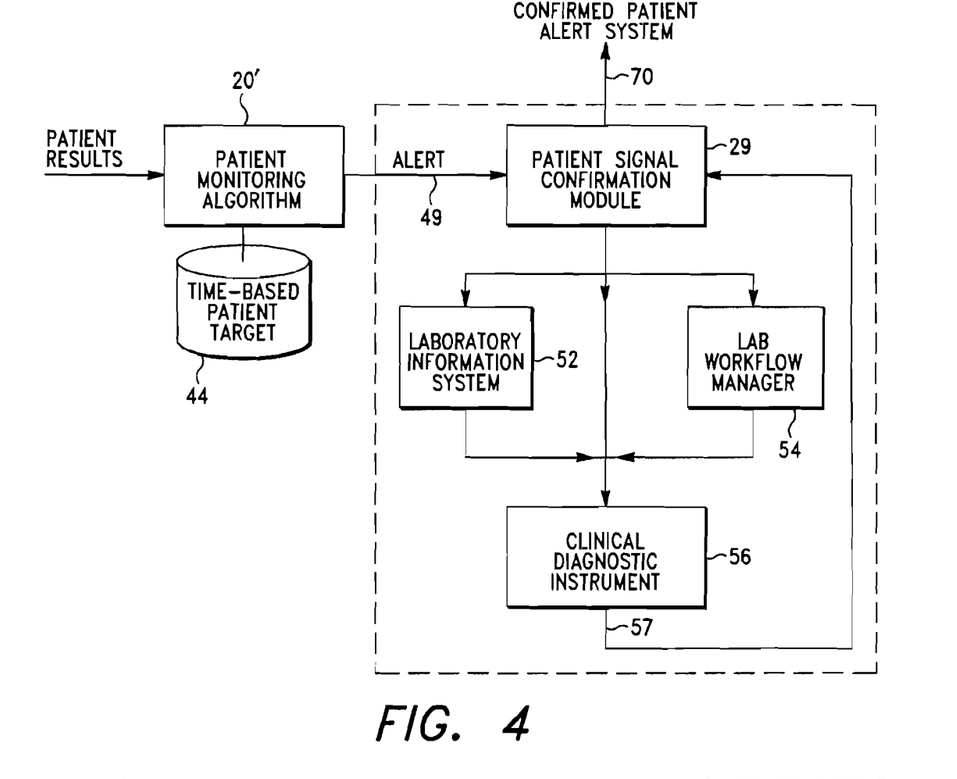
FIG. 4 depicts a block diagram of an automatic quality control system used in a clinical diagnostic process in accordance with an exemplary embodiment of the present invention.

The implementation and execution of the process of FIG. 3 running in application module 20 comprises a complete patient monitoring algorithm as described above and as depicted by element number 20' in FIG. 4. Looking to FIG. 4, any alert 49 generated by the patient monitoring algorithm 20' (i.e., any alert generated by the process of FIG. 3 implemented in application module 20) is directed to the patient signal confirmation module 29.

Figure 5:
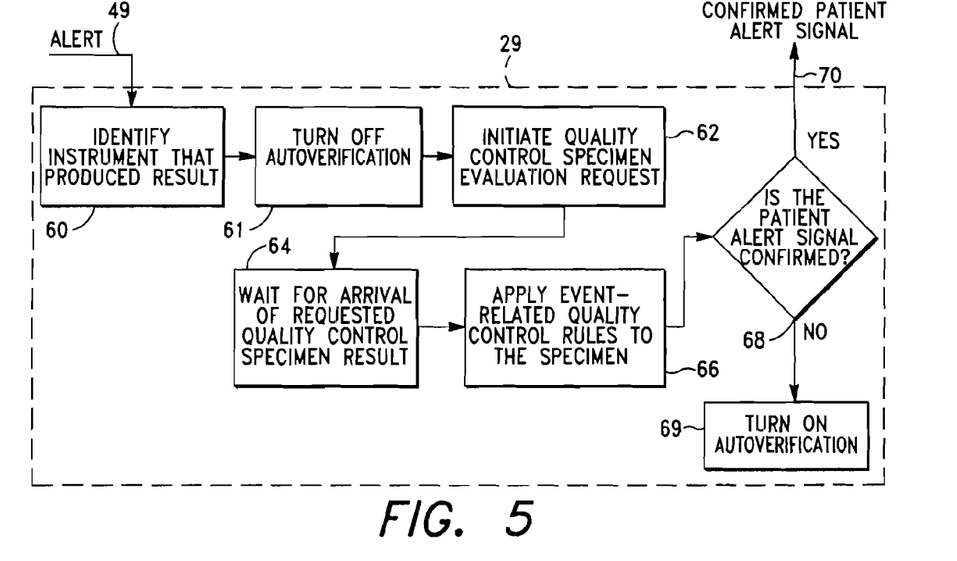
FIG. 5 depicts a detailed block diagram of the patient signal confirmation module of the automatic quality control system of FIG. 4.

The operation of the patient signal confirmation module 29 will now be described with reference to FIG. 4, showing module 29 in communication with a Laboratory Information System (LIS) 52, a lab workflow manager 54, and a clinical diagnostic instrument 56; and FIG. 5, showing the detailed flow and operation of the patient signal confirmation module. Turning first to FIG. 5, patient signal confirmation module 29 receives alert 49 and, at block 60 identifies the instrument that produced the result that caused the alert to be generated. The instrument is identified through the data associated with the test stored in database 48, or otherwise stored in memory or a media drive 44 of the client system 10 as previously described. At block 61, in the case of an instrument using autoverification of results, the autoverification function is turned off for that instrument while the validity of the alert signal is confirmed. Autoverification allows for results to be released as they are generated, based on predetermined condition(s) being met. Of course, if the identified instrument does not use autoverification, then no action is taken at block 61.

Upon identifying the instrument that produced the result, the process of module 29 initiates a quality control specimen evaluation request at block 62. Looking back to FIG. 4, depending upon the setup of the laboratory or system, the quality control specimen evaluation request is routed to any one of: (a) a Laboratory Information System (LIS) 52, (b) a lab workflow manager 54, or (c) directly to the clinical diagnostic instrument 56. As is known in the art, the request of any particular test for a specific diagnostic instrument may be scheduled via direct communication with the instrument or, more commonly, through a workflow manager or laboratory information system which are operable to receive the request and communicate with the diagnostic instrument according to the protocol established by the laboratory. Regardless of how the clinical diagnostic instrument 56 receives the request, the quality control specimen evaluation is performed when the instrument receives the instruction to do so. In the case of a clinical diagnostic instrument that has on-board QC storage capabilities, the request will preferably be processed as a priority run.

Turning back to FIG. 5, with the quality control specimen evaluation requested, at block 64 the process of module 29 waits for the results of the quality control specimen test from the clinical diagnostic instrument to be completed. Looking to FIG. 4, when the clinical diagnostic instrument 56 has completed the test, the results are routed back to the patient signal confirmation module 29 along path 57.

For clarity in the drawing of FIG. 4, not all of the possible paths of the quality control specimen test results back to module 29 are shown. It will be apparent to those skilled in the art, however, that the path of the results back to module 29 will depend upon the route by which the clinical diagnostic instrument 56 received the instructions to perform the quality control specimen test. For example, if the instructions to perform the test came through the laboratory information system 52, then the results of the test will preferably be routed back to module 29 through that system. And, if the instructions to perform the test came through the lab workflow manager 54, then the results will preferably be routed back to module 29 through that same workflow manager. In some cases, even when the request comes through a workflow manager or laboratory information system, the clinical diagnostic instrument may have the capability to route the results directly back to module 29 without reporting through the intervening system. These and other variations are contemplated by the present invention.

Turning again to FIG. 5, when the results of the quality control specimen test are received, at block 66 the module applies event-related quality control rules to the specimen. The event-related quality control rules are preferably selected from a predefined group of QC rules based on the event that produced the initial internal patient alert. Thus, the quality control rules applied to any particular results of a quality control specimen will vary depending upon what event generated the need to perform the QC test. Upon completion of the selected event-related quality control rules to the specimen results, at decision block 68 the module confirms or denies the validity of the initial internal alert—i.e., determines whether an actual limit was exceeded or if an out-of-control condition actually exists such that operator intervention is required.

If the validity of the initial internal patient alert signal is confirmed, the process provides a confirmed patient alert signal output 70 which notifies the operator of the condition. The alert signal can be any type of indicator, such as an alert tone, a light, a text message or graphic displayed on a display screen, or any combination thereof.

If the validity of the initial internal patient alert signal is not confirmed, then autoverification for the identified instrument is turned on (or in the case of an instrument that does not use autoverification as described above, no action is taken) at block 69, no alert to the operator is generated, the internal alert signal is reset, and the patient monitoring algorithm 20' continues to run with no indication to the operator of any exceeded limit, out-of-control condition, or other detectable problem.

Upon generation of a confirmed patient alert signal indicating that an error in fact exists, and if troubleshooting by the operator verifies that an error exists, corrective action takes place. For example, corrective action may include calibration, maintenance, reagent change, etc. Corrective action constitutes an "event" that triggers a statistical model which determines what control levels need to be tested and in what quantity (i.e., how many replicates) to verify corrective action and troubleshooting was effective. The system also determines the frequency of quality control testing and the levels to be tested, based on, for example, unplanned maintenance, precision, bias, unplanned reagent changes, unplanned calibrations and unplanned use of fresh controls. Bias and precision for each instrument is preferably continuously monitored by the system. EWMA, used in one embodiment to track patient data for maintenance/calibration, is also used as an error detection mechanism. In one embodiment, the system is sensitized to specific patient data populations, and patient data is filtered, e.g., truncated.

As can be seen, the system and method for automatic quality control of clinical diagnostic processes of the present invention provide improvements and advantages over known clinical diagnostic processes. The system and method as described and claimed herein monitors and checks internal patient alert signals and automatically instigates testing of a quality control specimen, applying event-related quality control rules, and providing an alert to the operator only upon confirmation of the validity of the internal alert signal. The automatic quality control system and method thus eliminates the uncertainty of operator reaction to an alert signal and implements the quality control run without operator intervention.

Patient Monitoring Algorithm

As briefly described previously, the process depicted in FIG. 3 implemented and executed as Biometric Quality Control process 20 as depicted in FIG. 1, together comprise a patient monitoring algorithm 20' as depicted in FIG. 4. As discussed above, while described in conjunction with a Biometric Quality Control process, the system and method for automatic quality control of clinical diagnostic processes of the present invention may equally be used in conjunction with other quality control processes. A more detailed description of the process of FIG. 3 will now be provided. As shown, the routine QC and patient data-based QC processes run simultaneously and in parallel. The biometric model requires configuration prior to use. In a first configuration step, parameters are set for the frequency and character (e.g., number of QC test samples) of routine QC testing for each test (e.g., analyte). In a second configuration step, the QC rule (e.g., 1 ks rule) is set for monitoring data generated by the routine QC process for each test. Another configuration step includes optimizing the QC rule (e.g., EWMA model) for monitoring data generated by routine QC testing for each test. Also, the QC rule (e.g., EWMA model) is optimized for monitoring variance of data generated by routine QC testing for each test. Another configuration step includes establishing a patient data QC protocol for each test, e.g., by truncating time-interval patient data and determining a mean and standard deviation of the remaining data population by hour of day and day of week. The QC rule (e.g., EWMA) is then optimized for accepting normalized patient data to monitor the analytical process for each test. Another configuration step includes setting parameters for confirmation testing for each test.

After the model is installed equilibration of the model is performed, e.g., by operating the model on new data for a period of time making adjustments to set parameters as appropriate. During operation of the model, QC materials are routinely tested for each test as required by the model. For example, a 1 ks rule is used in one aspect. If the 1 ks rule test fails, patient testing is halted, a root cause is established and/or corrective action is taken. Confirmation testing is performed, and patient testing resumes if confirmation testing passes. In another aspect, an EWMA rule is also applied to the routine QC data. If the EWMA rule fails, patient testing is halted, a root cause is established and/or corrective action is taken. In another aspect, an EWMA test for variance is applied to the data. If the EWMA variance test fails, patient testing is halted, a root cause is established and/or corrective action is taken.

On the patient QC side, patient data is normalized for each test according to the hour of day and day of week. An optimized EWMA model is then applied to the normalized data. If the EWMA model triggers an error signal, patient sample testing is halted and routine QC is performed as above. Whenever a defined event (e.g., change event) occurs during the course of a day, confirmation testing is performed.

According to one embodiment of the present invention, the Biometric QC application module 20 includes a module 26 configured to determine truncation limits for a patient population. In preferred aspects, truncation module 26 determines truncation limits using the following general steps:

1. Collect all patient results over a given period of time. For example, a minimum of 91 days worth of data is useful, but one year's worth of data or more is preferable.

2. Determine patient-result truncation limits. Patient-result truncation limits are preferably determined when setting up a laboratory and when there is a significant change in the system. Examples of significant changes include a change in the population the laboratory services, a change in a reagent formulation, or an observed change in the distribution of results. Determining truncation limits typically assumes that the percentage of the patient population to exclude has been determined. Two preferred processes for determining truncation limits include a) determining truncation limits equidistant from the median of the un-truncated population, and b) determining truncation limits that maximize the decrease in the standard deviation of the truncated population relative to the number of samples that are truncated (i.e., removed from the database). The second methodology is preferred, but the two methods may give similar results in many cases. In one embodiment, the second methodology is used as the primary process for determining truncation limits and the first methodology is used as a "sanity" check.

3. For each hour of the week, calculate the mean and the standard deviation of the truncated patient results.

4. Determine the optimal percentage of patient results to truncate for each analyte. It should be understood that although the steps are discussed in a given order, the steps are not necessarily performed in the order given. For example, step number 4 is preferably performed before Step number 2.

The patient results preferably contain complete days and complete weeks of data so that when the simulation "wraps," it wraps to the correct hour and the correct day of the week. In certain aspects, for each patient result, the minimum information required includes:

A unique instrument identifier (ID);

The date and time the instrument performed the result, e.g., date/time stamp;

The minimum and/or maximum reportable results for the analyte (e.g., any result less than the minimum is reported with a "<" and any result above the maximum is reported with a ">"); and The number of significant digits (nsd) to which patient results are rounded (e.g., 1, 0.1, 0.01, etc.).

An identifier or other information uniquely identifying the instrument from which the data is preferably provided. If multiple instruments of the same type are used, they can be treated as a single instrument if they all process similar patient samples. However if one instrument is used for stat requests and another for routine requests, or if one serves outpatient testing and another serves emergency department patients, etc., then the patient results for each instrument are preferably analyzed separately.

Most laboratory systems capture and store many different date/time stamps. Preferably, the date/time stamp associated with the time the instrument actually performed the test is provided to the system. However, the date/time stamp associated with when the test was ordered, when the sample was collected, when the sample was received in the lab, or when the result was verified, may be used. If the date/time the instrument performed the test is not available, the next best date/time is the one that comes closest to approximating the correct time order the results were tested on the instrument.

In labs that auto-verify results, result verification dates and times may not be a good choice. Results that fail auto-verification (which tend to be "abnormal" results) may include delayed verification times relative to results that pass auto-verification, messing up the time order of the results in a way that is correlated with the magnitude of the results, thereby creating apparent time series trends that don't really exist.

Results preferably cover complete days and complete weeks. Results collection can start any day of the week, but if there are 26 weeks of data that start on a Tuesday, then the last day should be the Monday that is 26*7=182 days later.

In certain aspects, it is preferred that a few extra hours of results at each end are included; that is, results would start a few hours before 12:00 AM Tuesday and end a few hours after 12:00 AM of the Tuesday that is 182 days later. This allows complete data for the first and last hour of the week when calculating patient result means and SDs by hour of the week using a moving window.

In one embodiment, the day of the week information is not necessary so long as the actual (calendar) date is provided. In certain aspects, for example, algorithms are used for determining the day of the week. For example in MATLAB the function weekday(date) returns a number between 1 and 7 denoting the day of the week (e.g., Sunday=1, . . . , Saturday=7) of the given date.

The minimum, maximum, and rounding factor (e.g., nsd) are preferably provided to the system, however such information can typically be inferred from the patient results themselves. It is generally safer to have the laboratory provide this information for each analyte. In order to utilize all of the patient data, patient results with a "<" are replaced with the minimum result−1*nsd, and results with a ">" are replaced with the maximum result+1*nsd.

As stated above, the nsd can usually be inferred from patient results; however, it is safer to have the laboratory provide this information for each analyte.

According to one embodiment, two processes are used to determine truncation limits to achieve the desired percentage of patient results that are outside truncation limits (pctout). In this embodiment, methodology 2 is preferably used as the primary method, and methodology 1 is used as a "sanity check." If the truncation limits from the two methods differ greatly, the cause should be investigated. It should be understood that each methodology may be used solely and separately. The two methodologies will now be discussed with reference to MATLAB functions and protocols, however it should be understood that other programming languages and applications may be used, for example, C, C++, Mathematica, Visual Basic, COBOL, PASCAL, FORTRAN, etc.

According to one embodiment, truncation limits equidistant from the median of the un-truncated population are determined as follows:

1. Determine the total number, Nres, of patient results (e.g., using MATLAB, if the patient results are stored in a vector named "result" then the function length(result) will return the number of results in the vector).

2. Calculate the median (med) of all Nres results (e.g., in MATLAB the function median(result) will calculate the median of the results in the vector result).

3. Calculate the set of unique absolute differences, uadisttomed, between each patient result and the median (e.g., in MATLAB the function abs(x) will calculate the absolute value of x and the function unique(x) will return a vector that contains exactly one occurrence of each unique value in the vector x).

4. For each value of uadisttomed: a. Determine the number of results, Nresout, whose absolute difference from the median, med, exceeds uadisttomed. b. Calculate the percent truncated, pctresout=Nresout/Nres.

5. Select, automatically or manually, the value of uadisttomed that gives the pctresout that is closest in value to the target, pctout.

6. Calculate the lower truncation limit, tlo=med−uadisttomed and the upper truncation limit, thi=med+uadisttomed using the selected value of uadisttomed.

According to one embodiment, truncation limits that maximize a decrease in the standard deviation of the truncated population relative to the number of samples that are truncated are determined as follows:

A. Calculate the SD of all patient results, for example:

1. Determine the total number, Nres, of patient results.

2. Calculate the standard deviation, SDres, of all the results (e.g., in MATLAB the function std(result) calculates the standard deviation of the results in the vector result).

B. Determine unique patient results, for example:

1. Determine all the unique values, ures, of the patient results.

2. Sort the unique values, ures, from smallest to largest (e.g., the MATLAB function unique(result) will return the unique result values in sorted order).

C. Initially set the truncation limits to the lowest and highest result and the percent truncated to zero, for example:
1. Let tlo=the smallest ures value.
2. Let thi=the largest ures value.
3. Set pctout=0.
D. Move in truncation limits from one tail and recalculate: Repeatedly move in (automatically or manually) the truncation limits from one or the other tail of the result distribution and recalculate the percent outside truncation limits until the percent outside truncation limits exceeds pctout, for example:
1. Count the number of results, Nrestlo, that equal tlo.
2. Count the number of results, Nresthi, that equal thi.
3. Calculate the standard deviation, SDrestlo, of the results that are greater than tlo and less than or equal to thi (include the results that equal tlo to those that are already excluded).
4. Calculate the standard deviation, SDresthi, of the results that are greater than or equal to tlo and <thi (include the results that equal thi to those that are already excluded).
5. Compare the value of (SDres−SDrestlo)/Nrestlo to the value of (SDres−SDresthi)/Nresthi.
E. Determine which tail gives the greater reduction (SDres−SDrestlo)/Nrestlo>(SDres−SDresthi)/Nresthi For example, if (SDres−SDrestlo)/Nrestlo>(SDres−SDresthi)/Nresthi then moving in the lower truncation limit produces the larger decrease in SDres relative to the number of samples lost due to truncation.
1. Replace tlo with the smallest value of ures that is >tlo.
2. Replace SDres with SDrestlo.

(SDres−SDrestlo)/Nrestlo<(SDres−SDresthi)/Nresthi

For example, if (SDres−SDrestlo)/Nrestlo<(SDres−SDresthi)/Nresthi then moving in the upper truncation limit produces the larger decrease in SDres relative to the number of samples lost due to truncation.
1. Replace thi with the largest value of ures that is <thi.
2. Replace SDres with SDresthi.
F. Determine the number of results, Nresout, that are less than tlo or greater than thi. (This calculation preferably includes all values, including replicates.)
G. Calculate the percent of results outside truncation limits
For example, pctresout=Nresout/Nres provides the percent of results outside truncation limits. When pctresout becomes greater than or equal to pctout, the corresponding (tlo,thi) pair gives pctresout>pctout and the (tlo,thi) pair at the step just prior gives pctresout<pctout. Select as the lower and upper truncation limits the (tlo,thi) pair that minimizes the absolute difference between pctresout and pctout. This is done by determining the first tL,tU pair, and that tL gives the larger SD decrease.

According to one embodiment, a calculation of the patient means and standard deviations (SDs) for each hour of the week is performed as follows:
Require that each moving window contains a minimum number of results. (e.g., twenty would be an adequate number, but forty or more would be better.)
Use a moving window of one hour±one hour (e.g., to create a three-hour window) whenever the window has at least the minimum number of results. Using a moving window smoothes the estimates of the means and SD and helps increase the sample sizes of the estimates.
If the one hour±one hour window has fewer than the minimum number of results, widen the window by including the results that are closest in time to the one hour±one hour window until the window contains at least the minimum number of values. For example, if the current window is 5 results short then find the 5 results closest in time to the current window and widen the window just enough to include these 5 results.

The calculations generally require the following input values: a collection of patient results within truncation limits, resin; the hour of the week, hrwk, for each result (e.g., hrwk ranges from 1 to 7*24=168); the week number, wkn, of the result (e.g., if there are 13 weeks of data in resin then wkn ranges from 1 to 13); and the half-width of the moving window, whlfwdth (e.g., in hours) used to calculate the means and standard deviations.

The calculations generally provide the following output results: Nresin(hrwk)—the number of results used in the calculations for hour of the week, hrwk; avgresin(hrwk)—the average of the results within the window for the hour; SDTresin(hrwk)—the total standard deviation for the hour; SDBresin(hrwk)—the week-to-week (between-week) standard deviation for the hour; and SDWresin(hrwk)—the within-week standard deviation for the hour.

According to one embodiment, a calculation is performed as follows for each hour of the week:
1. Determine the results, resin(hrwk) that are within the moving window for hour hrwk.
For the first whlfwdth hours of the week (hrwk=1 to whlfwdth), resin(hrwk) will be the results where hour of the week>hrwk−whlfwdth+168 or <hrwk+whlfwdth. (The left half of the window needs to "wrap").
For each hour between whlfwdth+1 and 168−whlfwdth, resin(hrwk) will be the results where hour of the week>hrwk−whlfwdth and <hrwk+whlfwdth.
For the last whlfwdth hours of the week (hrwk=168−whlfwdth+1 to 168), resin(hrwk) will be the results where hour of the week>whlfwdth−hrwk or <whlfwdth+hrwk−168. (The right half of the window has to "wrap")
2. Determine the number, Nresin(hrwk), of results defined by resin(hrwk).
3. Calculate the average, avgresin(hrwk) of the results defined by resin(hrwk).
4. Calculate the deviations devavgresin(hrwk)=resin(hrwk)−avgresin(hrwk).
5. Perform a one-way random effects analysis of variance (ANOVA) on the deviations devavgresin versus week number, wkn to obtain SDTresin, SDBresin, and SDWresin. For example, the MATLAB function [SDTresin,SDBresin,SDWresin]=sdtbw(devavgresin,wkn) can be used to perform the necessary ANOVA calculations.

In one embodiment, it is preferable to determine the truncation limits that minimize the worst case expected number of "bad" results produced or reported during an out-of-control error condition (ANPTE) over a wide range of error conditions. In general, a "bad" result is a result where the difference between the true concentration and the measured concentration exceeds the total allowable error specification (TEa). ANPTE should be measured by simulation. Therefore, determining analyte specific truncation limits based on worst-case ANPTE performance requires accurate simulation of the time-series characteristics of the patient results in order to calculate ANPTE for different sets of truncation limits and different magnitudes of out-of-control error conditions.

In certain aspects, implementing a patient-based quality control (QC) rule requires the following parameters:
Truncation limits—tlo and thi;
The average of patient results within trucation limits for each hour of the week—avgresin(hrwk);
The total standard deviation of patient results within truncation limits for each hour of the week—SDTresin(hrwk);

Number, Npat, of consecutive within-truncation-limits patient samples to average; and The two parameters that define the QC rule, for example:
w and q for the EWMA rule.
h and k for the CUSUM rule Note: In certain aspects, only the EWMA rule is implemented, however, the CUSUM rule may be implemented additionally or alternatively.

QC performance measures to evaluate a patient-based QC rule typically include:

ANPfr (The average number of patient results between false rejections);

ANPed(SE,RE), SE≠0, RE>1 (The average number of patient results to error detection when an out-of-control error condition with shift=SE and increase in stable analytic imprecision=RE exits)

ANPTE(SE,RE), SE≠0, RE>1 (The average number of "bad" results produced during an out-of-control error condition with shift=SE and increase in stable analytic imprecision=RE)

Ideally, one specifies a target ANPfr, and then selects the parameters that minimize the maximum (worst-case) value of ANPTE(SE,RE) over a wide range of out-of-control conditions. However, because the patient-based QC parameters are typically all inter-related, finding the "optimal" combination (including the "optimal" truncation limits) may be a complicated task. Accordingly, in one embodiment, determining truncation limits when using the EWMA rule is performed as follows:

1. Specify a target ANPfr for the patient-based QC rule;
2. Set Npat=1;
3. Select an EWMA parameter w that is optimal for detecting SE=TEa;
4. Find truncation limits that eliminate one or more of the following percentages of patient results: 0.5%, 1%, 2%, 5%, and 10%;
5. For each set of truncation limits:
    a. Calculate avgresin(hrwk) and SDTresin(hrwk);
    b. Find (by simulation) the EWMA parameter,q, that gives the target ANPfr;
    c. Calculate (by simulation) Peak=(ANPTE(-TEa)+ANPTE(TEa))/2; and
6. Select the truncation limits that minimize the value of Peak. This approach optimizes truncation limits for detecting SE errors but ignores the effect of RE error conditions. TEa can be given as either an absolute value or a percent. The published Ricos limits may be used.

According to one embodiment, a time-series bootstrap approach based on block resampling of consecutive sets of patient results over time is implemented by Biometric QC module 20 to simulate in-control, time-series patient results. The patient results (data) and their date/time stamps are utilized in the simulation. In this embodiment, data preferably covers complete days and complete weeks and is sorted by date and time (a few extra hours of patient results at the beginning and end is generally not desired in this case).

The simulation of in-control patient data proceeds as follows according to one embodiment:
1. Generate a random date and time within the date and time interval spanned by the patient data. The first date/time stamp in the patient database immediately following the random date/time marks the beginning point of the simulation.
2. Find all the results that proceed or follow this point in time by, for example, no more than W minutes (e.g., w=120 minutes).

3. If the number of results within ±w minutes of the current result is <10, then continue searching backward and forward in time until 10 results are identified.
4. Randomly sample one of the results within the ±w minute block. This is the first simulated patient result.
5. Move to the next date/time stamp and repeat the process.
6. Continue in this fashion until the QC rule rejects.

In this embodiment, one "tricky" part occurs when the simulation is near the beginning or ending date of the patient data, because the simulation needs to "wrap around" from the last date/time point to the first date/time point in the database. This is why it is preferred that the database contain complete days and complete weeks of data so that when the simulation wraps around it wraps to the correct hour of the day and day of the week.

The MATLAB function named simwin determines the points that are within the window for each of the observed values. This algorithm requires the 91-day vector of patient results with the day, hour, and minute of each result. The simwin function figures out ½ of the window width (w) for a moving window. Within the function, minimum assures that a minimum number of results in the window exist.

For example, using a minimum number of 10 and a window of ±120 minutes, if a particular window contains fewer than 10 results, the window is widened until the minimum number of results is obtained. This results in a 1 in 10 chance of sampling a particular result. Using this approach, the chances of sampling the exact same results is very small. For example, after 5 windows have been sampled, the chances of sampling the same results is approximately 10-5.

The input into the function simwin are a particular value for the window width (w) and the minimum number of samples in the window (minimum). The output of simwin produces two variables—rb and rn, where rb is the beginning row of the window (rows are associated with a particular date and time), and rn is the number of rows in the window. Together, rb and rn determine the window that defines the rows.

The algorithm uses a moving window of the results. The simulation takes actual laboratory results with date and time stamp, in order, by date and time, and figures out a window that is well defined and simulates the results but makes use of the time-distribution of the data. Using this approach, a very large number of data points can be simulated, for example, if 5,000 patient data points are used, an effective simulation of a database of 500 million data points can be performed.

In one embodiment, simulation of an out-of-control error condition is performed by Biometric QC application 20. Simulating an out-of-control error condition generally involves determining how to transform the distribution of patient results so that the mean and SD of the transformed distribution accurately manifests the out-of-control error condition. The fact that the patient result data used in the simulations are typically rounded may cause some problems when trying to accurately simulate an out-of-control error condition. According to one embodiment, a strategy is provided for creating an out-of-control result distribution to overcome the problems associated with rounding as follows:

1. For result, x, first "unround" the result by adding a uniformly distributed random number between ±0.5*nsd to x; call it xT.
2. Next, add SE(xT) to xT, where SE(xT) is the magnitude of the out-of-control error condition at concentration xT.
3. Next, round the result to nsd digits. If the out-of-control result is outside the minimum or maximum reportable results, replace it with the minimum−1*nsd or maximum+1*nsd respectively.

In certain aspects, when simulating SE error conditions, if the total allowable error specification (TEa) for the analyte is given as a constant, it is preferred to specify SE as a constant, and if TEa is given as proportional to concentration, to specify SE as proportional to concentration. Unlike simulations of control QC strategies, both negative and positive SE error conditions are preferably simulated because the non-normal distributional characteristics of the patient distributions mean that symmetrical behavior between positive and negative error conditions can't be expected.

It is preferred that SE range between ±2TEa. Also, any combination of SE and RE error is preferably handled in the following way:

1. Unround as above.
2. Next, multiply the unrounded result by a normally distributed random number with mean=0 and variance=(RE2 1)*SD(xT), where SD(xT) is the stable analytic imprecision at concentration xT and RE is the magnitude of the increase in imprecision given in multiples of stable analytic SD.
3. Next, add SE(xT) and round to nsd digits as before.

Simulating the out-of-control time series characteristics of patient results proceeds in the same way as for in-control results except that an out-of-control result is randomly sampled from the ±w minute block of transformed results on either side of the current date/time stamp.

According to one embodiment of the present invention, the Biometric QC application module 20 includes a QC Confirmation Testing module 28 configured to determine an optimal QC rule (and associated number of QC samples) needed to confirm that the analytical process is still in control after an event has occurred. The optimal rule minimizes the worst case probability of producing "bad" results (pQE) because of an error condition associated with the event. In preferred aspects, the QC Confirmation Testing module 28 determines an optimal QC rule using the following general steps.

Step 1—Identify a relevant performance measure. According to one embodiment, the algorithm includes a module configured to determine an optimal QC rule (and associated number of QC samples) needed to confirm that the analytical process is still in control after an event has occurred. In one embodiment, the optimal rule to be determined should minimize the worst-case probability of producing "bad" results (pQE) because of an error-condition associated with the event.

This approach is consistent with the basic approach for routine QC tests, except that for routine QC testing an error occurring is modeled at some point in time and then it is determined how many samples are needed to detect the condition.

Step 2—Select a QC rule The $\bar{X}$/S rule is preferably used, because it has been shown that the $\bar{X}$/S rule is the best QC rule for testing a single group of QC samples. (See, e.g., Parvin C A. New insight into the comparative power of quality-control rules that use control observations within a single analytical run. Clin Chem 1993; 39:440-7).

Step 3—Determine the pQE. Two probabilities are required to calculate the probability of producing a bad result (pQE): 1) the probability of producing a bad result due to an out-of-control error condition (dpE), and 2) the probability of error detection (ped). The pQE is equal to the increase in the probability of producing "bad" results because of the error condition multiplied by the probability of failing to detect the error condition, as given in the following formula: pQE= dpE*(1−ped). Using this approach, the probability of producing a "bad" result (pQE) can be determined when using a specific QC rule after an event.

Step 4—Vary error limits to minimize pQE. When choosing the QC rule to use after an "event", it is desirable to minimize the worst-case probability of producing "bad" results because of an error-condition associated with the "event."

Step 5—Vary rejection limits to guarantee that pQE is never >5%. In this step, $\bar{X}$ and S rejection limits are varied and the number of QC samples over a range of total allowable error specifications (TEa) and false rejection rates (pfr) are varied to guarantee that the pQE never exceeds 5%, regardless of the error condition. It should be appreciated that the selection of 5% for the pQE was arbitrary, and it could be smaller or larger as desired. In addition, the number of QC samples is restricted to multiples of two, which is generally the number of samples that labs run for general chemistry tests.

The algorithm is preferably configured to consider out-of-control error conditions that result in a shift from target values (SE), an increase in stable analytic imprecision (RE), and/or an increase in both SE and RE.

EVALUATING THE X BAR/S RULE. According to one embodiment, a single $\bar{X}$/S rule is preferably used. In certain aspects, an $\bar{X}$ rejection limit of 2.43 and an S rejection limit of 3.53 are used to obtain a 1 in 1000 probability of rejection. It should be understood that other rejection limits may be used. To evaluate the $\bar{X}$ value, according to one embodiment, z scores for each of the two QC values are created and averaged. An average z score with absolute value greater than 2.43 is a rejection. To evaluate the S value, the SD of the two z scores is calculated and an SD greater than 3.53 is a rejection.

When choosing a QC rule to use after an "event", it is desirable to minimize the worst-case probability of producing "bad" results because of an error-condition associated with the "event". The probability of producing "bad" results subsequent to an "event" is a function of the probability of producing "bad" results because of the error condition and the probability of failing to detect the error condition.

In step 4, the rejection limits of $\bar{X}$ and SD values are varied to determine the values that produce the smallest pQE. As the $\bar{X}$ and SD values are varied, the relative power for detecting a shift in the mean or an increase in imprecision varies.

In step 5, using an embodiment of the present invention, the number of QC samples required after an event can be determined by varying total allowable error specifications (TEa) and false rejection rates (pfr). If event-related QC fails to detect the out-of-control error condition, how long the error condition will persist and, consequently, the number of bad results reported will be a function of the routine QC testing strategy and will depend on the average number of patient samples to error detection (ANPed). (See, e.g., Ye, Jay et. al. Performance Evaluation and Planning for Patient-Based Quality Control Procedures. Amm J Clin Pathol 2000:113: 240-248).

The expected number of bad results due to the event is equal to the pQE surface multiplied times the ANPed. For example, if the ANPed is 20 and the pQE is never allowed to exceed 5%, the expected number of bad results will never exceed 20*0.5 or 1 bad result, which is probably acceptable. However, if the ANPed is 200, the expected number of bad results will be 10. Whether or not this is acceptable depends on factors such as the probability of this error condition occurring. For example, if the "event" is daily instrument maintenance and the pfr is 1:500, then the likelihood of a pfr associated with daily maintenance is less than once a year. Because the cost of a pfr is probably high, labs will probably want to make the pfr as small as possible. (pfr costs generally include running additional QC samples, additional maintenance, delay in reporting patient results, etc.)

According to one embodiment, the system is configured so that it is also possible to set the number of QC samples tested to a continuous value. This allows N to range from 2 to any number. In one embodiment, this is done using a 2 stage testing approach: initially test 2 QC samples and depending on the values of these 2 samples either accept and assume that the testing system is okay and immediately test additional QC samples. For example, the first 2 QC samples are not accepted and 2 additional samples are immediately tested, a QC rule based on the 4 samples combined is needed. In this case, the number of QC samples tested is a random variable based on whether the first pair of QC samples is accepted or rejected. Using this strategy, it is possible to determine the smallest N that results in a pQE of, e.g., exactly 0.05. It is fairly common practice in the laboratory to repeat out-of-range control samples, and if the repeat controls are within range, to accept them and continue testing.

Such an approach has been disparaged in the past, based mainly on comments by Dr. Westgard which stressed that repeating QC samples is not improving the lab's QC, but rather is lowering the false rejection probability and error detection ability. This is only correct if the rejection limits for the two QC tests are not adjusted so that the overall false rejection probability remains as desired. If the QC rules applied to the first and second set of QC samples, and the false rejection probability associated with the first and second samples are both allowed to vary then this approach is more powerful than just testing a single set of QC samples.

This supplemental approach has several advantages over the mean/range ($\overline{X}$/S) rule. For example, it will generally provide better results, on average, than the mean range rule at detecting error when using the same number of QC samples. Additionally, it is advantageous to have the flexibility to set the number of QC samples to any number. This is particularly useful with tri-level controls where the number of QC samples are in multiples of 3.

Additional aspects of the invention, together with the advantages and novel features appurtenant thereto as be set forth in part in the description herein, in part will become apparent to those skilled in the art upon examination of the description, or may be learned from the practice of the invention. The objects and advantages of the invention may be realized and attained by means of the instrumentalities and combinations particularly pointed out in the appended claims.

What is claimed and desired to be secured by Letters Patent is as follows:

1. A computer-implemented method of providing automatic quality control of a clinical diagnostic process, comprising:
    acquiring test data from one or more laboratory instruments;
    analyzing said test data by applying a patient monitoring rule to said test data;
    generating an internal alert signal when said test data exceeds a predetermined error threshold as calculated by said patient monitoring rule;
    applying a confirmation rule to said test data in response to said internal alert signal; and
    generating an operator alert signal if said confirmation rule confirms said internal alert signal as valid.

2. The method of claim 1, wherein said applying a confirmation rule comprises:
    identifying a laboratory instrument that produced a result exceeding said error threshold;
    instructing said identified laboratory instrument to test a quality control specimen and to generate test results; and
    applying event-related quality control rules to said generated test results.

3. The method of claim 1, further comprising the step of: waiting for said generated test results.

4. The method of claim 1, wherein said test data comprises patient data.

5. The method of claim 1, wherein said patient monitoring rule comprises a Biometric Quality Control process, an EWMA rule, a CUSUM rule, or combinations thereof.

6. A computer-implemented method of providing automatic quality control of a clinical diagnostic process, comprising:
    acquiring patient data from one or more laboratory diagnostic instruments;
    applying a Biometric Quality Control process to said patient data;
    generating an internal alert signal when said patient data exceeds an error level as determined by said Biometric Quality Control process; and
    confirming a validity of said internal alert signal by automatically performing a quality control check.

7. The method of claim 6, wherein said automatically performing a quality control check comprises:
    identifying a laboratory instrument that produced a result exceeding said error level;
    initiating testing of a quality control specimen on said identified laboratory instrument;
    waiting for results from said testing of a quality control specimen;
    applying event-related quality control rules to said results to determine whether said instrument is operating within an expected tolerance; and
    generating an operator alert signal if said instrument is not operating with said expected tolerance.

8. A computer-implemented method of providing automatic quality control of a clinical diagnostic process, comprising:
    acquiring patient data from one or more laboratory clinical diagnostic instruments;
    analyzing said patient data by applying a patient monitoring rule to said patient data;
    automatically performing a test of a quality control specimen when said patient data exceeds a predetermined error level.

9. The method of claim 8, further comprising:
    generating an operator alert signal if said test of a quality control specimen indicates an out of tolerance condition.

10. The method of claim 8, wherein said patient monitoring rule comprises a Biometric Quality Control process.

11. The method of claim 8, wherein said automatically performing a test of a quality control specimen comprises:
    identifying a laboratory clinical diagnostic instrument that produced a result exceeding said error level; and
    performing an evaluation of a quality control specimen on said identified laboratory clinical diagnostic instrument.

12. A system for providing automatic quality control of a clinical diagnostic process, comprising:
    one more laboratory instruments operable to acquire test data;
    a computer system operable to communicate with and receive test data from said laboratory instruments, said computer system having a processor operable to:
        apply a patient monitoring rule to said test data;
        generate an internal alert signal when said test data exceeds a predetermined error threshold as calculated by said patient monitoring rule;

apply a confirmation rule to said test data in response to said internal alert signal; and generate an external operator alert signal if said confirmation rule confirms said internal alert signal as valid.

13. The system of claim 12, wherein said applying a confirmation rule comprises:

identifying a specific laboratory instrument that produced a result exceeding said error threshold;

instructing said identified laboratory instrument to test a quality control specimen and to generate test results; and applying event-related quality control rules to said generated test results.

14. The system of claim 12, wherein said patient monitoring rule comprises a Biometric Quality Control process, an EWMA rule, a CUSUM rule, or combinations thereof.

15. The system of claim 12, wherein said external operator alert signal comprises a visible light, an audible sound, text on a display screen, an image on a display screen, or combinations thereof.

16. A system for providing automatic quality control of a clinical diagnostic process, comprising:

a computer system operable to communicate with and receive test data from one or more laboratory instruments, said computer system having a processor operable to:

apply a monitoring rule to said test data;

automatically instruct a laboratory instrument to perform a test of a quality control specimen when said data exceeds a predetermined error level.

17. The system of claim 16, wherein said processor is further operable to:

generate an operator alert signal if said automatic test of a quality control specimen indicates an out of tolerance condition.

18. The system of claim 16, wherein said processor is further operable to:

apply event-related quality control rules to results of said test of a quality control specimen.

19. The system of claim 16, wherein said monitoring rule comprises a Biometric Quality Control process.

20. A computer-implemented method of providing automatic quality control of a clinical diagnostic process, comprising:

acquiring test data from one or more laboratory instruments;

analyzing said test data by applying a quality control rule to said test data;

generating an internal alert signal when said test data exceeds a predetermined error threshold as calculated by said quality control rule;

applying a confirmation rule to said test data in response to said internal alert signal; and generating an operator alert signal if said confirmation rule confirms said internal alert signal as valid.

21. The method of claim 20, wherein said applying a confirmation rule comprises:

identifying a laboratory instrument that produced a result exceeding said error threshold;

instructing said identified laboratory instrument to test a quality control specimen and to generate test results; and applying event-related quality control rules to said generated test results.

22. The method of claim 20, further comprising the step of: waiting for said generated test results.

23. A computer-implemented method of providing automatic quality control of a clinical diagnostic process, comprising:

acquiring test data from one or more laboratory instruments;

analyzing said test data by applying a diagnostic rule to said test data;

generating an internal alert signal when said test data exceeds a predetermined error threshold as calculated by said diagnostic rule;

applying a confirmation rule to said test data in response to said internal alert signal; and generating an operator alert signal if said confirmation rule confirms said internal alert signal as valid.

24. The method of claim 23, wherein said applying a confirmation rule comprises:

identifying a laboratory instrument that produced a result exceeding said error threshold;

instructing said identified laboratory instrument to test a quality control specimen and to generate test results; and applying event-related quality control rules to said generated test results.

25. The method of claim 23, further comprising the step of: waiting for said generated test results.

* * * * *